United States Patent [19]

Lussenhop et al.

[11] Patent Number: 5,248,768
[45] Date of Patent: Sep. 28, 1993

[54] IMMUNOGENIC GLYCOPROTEINS OF HUMAN CYTOMEGALOVIRUS

[75] Inventors: Nancy O. Lussenhop, St. Paul; Bruce E. Kari, Minneapolis; Richard C. Gehrz, Mendota Heights, all of Minn.

[73] Assignee: The Children's Hospital, Incorporated, St. Paul, Minn.

[21] Appl. No.: 724,497

[22] Filed: Jun. 26, 1991

Related U.S. Application Data

[63] Continuation of Ser. No. 546,665, Jun. 29, 1990, abandoned, which is a continuation of Ser. No. 933,789, Nov. 24, 1986, abandoned.

[51] Int. Cl.$^5$ .................. C07K 15/04; C07K 15/14
[52] U.S. Cl. .................................. 530/395; 530/413; 530/388.3; 530/806; 530/809; 424/89
[58] Field of Search ............ 530/395, 413, 350, 806, 530/809, 388.3; 424/89

[56] References Cited

U.S. PATENT DOCUMENTS

| | | | |
|---|---|---|---|
| 3,959,466 | 5/1976 | Plotkin | 424/89 |
| 4,689,225 | 8/1987 | Pereira | 424/89 |
| 4,716,104 | 12/1987 | Harris et al. | 436/518 |
| 4,743,562 | 5/1988 | Rasmussen et al. | 424/89 |
| 4,783,399 | 11/1988 | Oldstone et al. | 436/548 |
| 4,808,518 | 2/1989 | Dorsett et al. | 436/543 |
| 4,818,678 | 4/1989 | Oldstone et al. | 436/548 |
| 5,124,440 | 6/1992 | Gehrz et al. | 530/395 |

FOREIGN PATENT DOCUMENTS

| | | | |
|---|---|---|---|
| 0122841 | 10/1984 | European Pat. Off. | |
| 180266 | 7/1986 | European Pat. Off. | 39/245 |
| 0198086 | 10/1986 | European Pat. Off. | |
| 0236145 | 9/1987 | European Pat. Off. | |

OTHER PUBLICATIONS

Britt et al., *Virus Research*, 4, 31–36 (1985).
Clark et al., *J. Virology*, 49, 279–282 (1984).
Forman et al., *J. Immunology*, 134, 3391–3395 (May, 1985).
Furukawa et al., *Proc. Soc. Exp. Biol. Med.*, 175, 243–250 (194).
Goldstein et al., *Infection and Immunity*, 38, 273–281 (1982).
Irmiere et al., *J. Virology*, 56, 277–283 (Oct. 1985).
Nowak et al., *Virology*, 132, 325–338 (1984).
Nowak et al., *Virology*, 134, 91–102 (1984).
Pande et al., *Proc. Natl. Acad. Sci. USA*, 81, 4965–4969 (1984).
Re et al., *J. Gen. Virol.*, 66, 2507–2511 (1985).
L. Rasmussen et al., *J. Virol.*, 55, 274 (1985).
W. J. Britt et al., *J. Virol.*, 58, 1985 (1986).
G. Farrar et al., *J. Gen. Virol.*, 67, 1467 (1986).
K. S. Kim et al., *J. Clin. Microbiol.*, 24, 474 (1986).
Y. I. Matsumoto et al., *Biochem. Biophys. Res. Commun.*, 137, 273 (1986).
F. R. Cockerill III, *Mayo Clin. Prac.*, 60, 636 (1985).
Schuster et al., *Mayo Clin. Prac.*, 60, 577 (1985).
Rasmussen et al., *Proc. Nat'l., Acad. Sci. USA*, 81, 876 (1984).
Rasmussen et al., *Journal of Virology*, 55, 274 (1985).
Kim et al., *Journal of Virology*, 20, 604 (1976).
Kim et al., *Journal of Clinical Microbiology*, 18, 331 (1983).
Welling et al., *Journal of Chromotography*, 297, 101 (1984).

(List continued on next page.)

"Human Cytomegalovirusspefic Cytotoxic T. Cells", pp. 919–931.

*Primary Examiner*—Robert J. Hill, Jr.
*Assistant Examiner*—Shelly Guest Cermak
*Attorney, Agent, or Firm*—Merchant, Gould, Smith, Edell, Welter & Schmidt

[57] ABSTRACT

Glycopeptides of human cytomegalovirus have been isolated and purified. These glycopeptides and antibodies reactive with them are useful in diagnosis and therapy.

3 Claims, 3 Drawing Sheets

OTHER PUBLICATIONS

Britt, *Virology*, 135, 369 (1984).
Law et al., *Journal of Medical Virology*, 17, 255 (1985).
L. Pereira et al., *Infection and Immunity*, 36, 924 (1982).
B. Kari et al., *J. Virology*, 60, 345 (Nov. 1986).
*Journal of General Virology*, vol. 69, 1988 SGM (GB), D. R. Greten et al.: "Characterization of attuman cytomegalovirus Glycoprotein Complex (GCI)", pp. 1205–1215.
*Virology*, vol. 167, 1988, Academic Press, Inc., R. R. Spaete et al.: "Human Cytomegalovirus Strain Towne Glycoprotein B Is Processed by Proteolytic Cleavage", pp. 207–225.
*The EMBO Journal*, vol. 5, No. 11, 1986, IRL Press Limited, (Oxford, GB), M. P. Cranage et al.: "Identification of the Human Cytomegalovirus Glycoprotein B. Gene and Induction of Neutralizing Antibodies via its Expression in Recombinant Vaccina Virus", pp. 3057–3063.
Journal Exp. Medicine, vol. 168, Sep. 1988, The Rockefeller University Press, L. K. Borysiewicz et al.:

1    2

93,000—

—50-52,000

GLP-A    GLP-B

5,248,768

IMMUNOGENIC GLYCOPROTEINS OF HUMAN CYTOMEGALOVIRUS

STATEMENT REGARDING FEDERALLY SPONSORED RESEARCH

This invention was made with government support from the Department of Health and Human Services, Grant Number: HDMC 5 P01 HD19937-03 GT. The government may have certain rights in the invention.

This is a continuation, of application Ser. No. 07/546,665 filed Jun. 29, 1990, now abandoned, which is a continuation of application Ser. No. 06/933,789, filed Nov. 24, 1986, now abandoned.

FIELD OF THE INVENTION

This invention relates to human cytomegalovirus (HCMV), in particular to glycopeptide components thereof, which are capable of eliciting an immune response. These glycopeptides and antibodies reactive with them are useful in diagnosis and therapy.

BACKGROUND OF THE INVENTION

Human cytomegalovirus has been associated with a number of clinical syndromes. The infection is usually asymptomatic and self-limiting in the immunocompetent child or adult, but can cause severe congenital disease in the fetus or infant and morbidity and mortality in immuno-compromised patients. HCMV is a common cause of mental retardation in children who acquire the infection in utero from mothers carrying an active infection, and is considered the leading opportunistic infection causing complications in immunosuppressed transplant patients. HCMV is also an important consideration in the treatment of Acquired Immunodeficiency Syndrome (AIDS). It has recently been suggested that HCMV is the causative agent in Kaposi's sarcoma, a cancer often seen in AIDS.

Much work has been done in recent years on the basic nature of HCMV in order to ameliorate these problems. HCMV is a virus of the herpes type, composed of a nuclear complex of nucleic acid and proteins, internal capsid proteins with structural or enzymatic functions and an external membrane envelope, containing glycopeptides and glycolipids. The first two groups are sequestered within the virion and may not be available in the intact, infectious virion to react with the immune system or antibodies. Furthermore, their presence in bodily fluids is not diagnostic of active infections as it is typical of herpes-type infections to go into a quiescent phase, where viral products are produced but infectious virions are not released. In the same manner, an initial infection may be abortive, i.e., the host cells begin to produce viral products, but these products are not assembled into virions so that active infection is never established.

HCMV can be diagnosed by one or more of the following methods: 1) identification of HCMV in virion bodies or CMV antigens in infected tissues by using indirect immunofluorescent microscopy, 2) detection of the virus in cell monolayers inoculated with infectious tissue or body fluids, 3) identification of HCMV-specific antibody in serum or, 4) hybridization with a complementary-labeled DNA fragment. For a review of current methods of diagnosing HCMV, see Mayo Report (*Mayo Clin. Prac.*, 60, 636, (1985)).

The most common method of diagnosing HCMV has been culturing the sample in human fibroblasts and inspection for typical cytopathic effects. This method has the advantage of being useful with a number of different, easily obtainable samples such as urine, throat washings or blood. After two to four weeks of growth, cultures can be inspected for evidence of HCMV infection, such as inclusion bodies or the typical giant, fused cell. This method has the disadvantage of requiring up to one month before diagnosis is confirmed.

Diagnosis utilizing monoclonal antibodies (MoAbs), using ELISA or direct immunofluorescence has been attempted. For example, Schuster et al. (*Mayo Clin. Proc.*, 60, 577-585 (1985)) have produced MoAbs to early and late HCMV nuclear proteins for use in immunofluorescence. The MoAb can be labeled with a fluorescent material and binding to intracellular HCMV in biopsy specimens or cultured cells can be observed. This kind of diagnosis is much more rapid than the culture method. Results may be available in less than one day.

Emerging antiviral therapies may become useful in treating HCMV infections. In the case of transplant patients, the immunosuppressant drug regimen can be altered to allow reactivation of latent HCMV. Furthermore, the symptoms of HCMV may mimic and therefore mask rejection so that control of transplant rejection requires accurate and rapid diagnosis of possible HCMV-active infections.

Antibodies against viruses can be injected directly into the circulation of HCMV patients, where the antibodies will bind to circulating virions and render them incapable of infecting host cells, thereby directly limiting the infection.

Additionally, nonexposed adults, especially females of childbearing age, may advantageously be administered a vaccine to confer protection from HCMV infection. U.S. Pat. No. 3,959,466 describes such a vaccine, using attenuated HCMV which is passed at least 50 and preferably 125 to 150 times through culture in human lung fibroblasts. Such vaccine is said to induce immunity against HCMV without allowing spread of the virus through the body. However, it is well known in the art that such attenuated viral vaccines, as well as "killed" vaccines, may have a certain low incidence of reversion to a virulent form. This has been well noted in the case of the Salk and Sabin polio vaccines.

Recently, subunit vaccines have been successfully constructed. Such subunit vaccine consists of only a portion of the virus and is not capable of causing the production of active virus. Alternatively, genetic material coding for immunogenic gene products can be spliced to a nonvirulent carrier virus, such as Vaccinia. The recombinant virus has the advantage of being reproduced for a time within the body, therefore stimulating immunity to a greater extent than can a killed virus.

It is becoming increasingly clear that the research on the immunology of HCMV must look to the membrane envelope components, especially the glycopeptides, as immunogens and markers of active HCMV infection. The starting material for a virus preparation includes, in addition to the desired membrane envelope components, host cell debris, nuclear proteins, capsid proteins and precursor peptides which are not found in the mature, infective virion. Even among the membrane envelope glycopeptides, not all are physically accessible to the immune system because they may reside in a fold or crypt or be sterically hindered from interaction with host immune responsive cells.

Therefore, it is desirable to provide a membrane envelope glycopeptide that is physically accessible to interaction with the immune system and with antibodies raised to it, in addition to eliciting antibodies with good in vitro reactivity, e.g., with respect to their binding to the glycopeptide. When such a glycopeptide on the surface of a virion reacts with its corresponding antibody, the virion is rendered incapable of infecting the host cell, that is, it is neutralized.

Such a glycopeptide and antibodies raised against it are useful in diagnosing active HCMV infections, treating such infections and, as a component of combined or subunit vaccines, for preventing infection in susceptible populations.

Before such antibody therapy, diagnosis of active HCMV infection or vaccine can be made available, it is necessary to identify and provide those compositions which stimulate humoral and cellular immunity. The glycopeptides of HCMV and other viruses have proved useful in this respect. For example, detergent extracts of HCMV containing certain membrane envelope glycopeptides can induce humoral and cellular immunity in the guinea pig. MoAbs have been obtained which immunoprecipitate glycopeptides with molecular weights of 50,000-58,000, 93,000 and 130,000 daltons that were associated in disulfide complexes. Some of these antibodies were observed to have neutralizing activity in vitro but only in the presence of complement. Only one MoAb, which reacted with an 86,000 dalton protein of HCMV was neutralizing in the absence of complement (Rasmussen et al., *Proc. Natl. Acad. Sci. U.S.A.*, 81, 876-880 (1984)).

In 1976, Kim et al. (*J. Virol.*, 20, 604-611 (1976)) were able to find at least 33 polypeptides in HCMV, ranging in size from 11,000 to 290,000 daltons. Six of these were shown to be glycopeptides, but the resolution technique, electrophoresis in non-reducing detergent gel, did not resolve these glycopeptides sufficiently to allow characterization of the individual molecules. One viral protein, a glycosylated protein of molecular weight 66,000 was found to be the most abundant viral polypeptide. Kim later succeeded in partially purifying this glycopeptide and raising MoAbs against it. However, none of his MoAbs was capable of neutralizing HCMV even at very high concentration. A mixture of nine MoAbs also failed to exhibit virus-neutralizing activity (Kim et al., *J. Clin. Microbiol.* 18, 331-343, 1983).

Therefore, a need exists for providing those HCMV glycopeptides capable of eliciting a protective humoral response. An additional needs exists for MoAbs directed against such glycopeptides.

BRIEF DESCRIPTION OF THE INVENTION

The present invention is directed to compositions of matter which are substantially-pure immunogenic glycopeptides which are preferably derived from HCMV. These glycopeptides are found on only the membrane envelope of the intact HCMV virion, where they are associated with other envelope glycopeptides via disulfide linkages. The glycopeptides are physically accessible to the immune system and to antibodies, and are capable of stimulating both humoral and cellular immunity in humans.

One embodiment of this invention comprises such a glycopeptide, herein termed GLP-A, which has a molecular weight of about 93,000 daltons. GLP-A comprises determinants which react with monoclonal antibodies, which antibodies react with HCMV but do not react with *Herpes simplex*, adenovirus, Epstein Barr virus or Varicella virus, and which antibodies are capable of neutralizing HCMV, preferably in the presence of complement.

A second embodiment of this invention comprises another such glycopeptide, herein term GLP-B, which has a molecular weight of about 50,000 to 52,000 daltons. GLP-B comprises determinants which react with monoclonal antibodies, which antibodies react with HCMV, *Herpes simplex* and adenovirus and which antibodies are capable to neutralizing HCMV in the absence of complement.

To obtain the glycopeptides of the present invention, HCMV from primary clinical isolates or such established strains as Towne or Toledo are first grown in a human cell, most conveniently, primary skin fibroblast cultures. Intact virions shed from the cell accumulate in the supernatant fluid, from which they may be concentrated by any standard means, preferably differential centrifugation followed by sucrose gradient centrifugation. The membrane envelope is stripped from the virion and the disulfide-linked glycopeptide complexes are further purified by high pressure liquid chromatography through an anion exchanger. Immunoprecipitation of the glycopeptide complexes, followed by reduction of the disulfide linkages, alkylation and gel filtration HPLC yielded the substantially-pure glycopeptides of the present invention.

Therefore, as used herein, the term "substantially-pure" is intended to mean that the glycopeptide complexes or the glycopeptides have been extracted from their natural association on the membrane envelope of HCMV with other membrane components and from internal nuclear or capsid components of HCMV. The procedures of the present invention readily afford a method for producing and purifying polypeptides or polypeptide complexes containing varying degrees of glycosylation, all of which are useful in the production of neutralizing MoAbs and which are also useful for the diagnosis of active HCMV infections.

The glycopeptides may be used to immunize mice in the first step of the well-known Kohler-Milstein method for producing monoclonal antibodies. More conveniently, a composition comprising whole HCMV virions may also be so used. Thus, the present invention also comprises MoAbs which bind to determinants present on GLP-A and GLP-B. Preferred MoAbs of the invention can neutralize HCMV, and can provide the basis for a diagnostic test for intact virions.

Therefore, the present invention is directed to a monoclonal antibody produced by a process comprising:

(a) immunizing a mouse with HCMV virions;
(b) fusing spleen cells from said mouse with cells from a myeloma line to produce hybridomas;
(c) selecting from said hybridomas a hybridoma which produces a monoclonal antibody which is reactive with HCMV, but does not react with *Herpes simplex*, adenovirus, Epstein Barr virus or Varicella virus, and wherein said monoclonal antibody is capable of neutralizing HCMV; and
(d) clonally expanding said hybridoma.

The present invention is also directed to a monoclonal antibody produced by a process comprising:

(a) immunizing a mouse with a HCMV virions;
(b) fusing spleen cells from said mouse with cells from a myeloma line to produce hybridomas;

(c) selecting from said hybridomas a hybridoma which produces a monoclonal antibody which is reactive with HCMV, *Herpes simplex* and adenovirus and which antibody is capable of neutralizing HCMV in the absence of complement; and (d) clonally expanding said hybridoma.

BRIEF DESCRIPTION OF THE DRAWINGS

FIG. 1A is a profile of radioactivity obtained by ion-exchange HPLC of unreduced [$^3$H]glucosamine-labeled strain Towne HCMV extract.

FIG. 1B is a profile of unreduced glycopeptides from peaks 1-4, as shown in FIG. 1A, that were examined by electrophoresis without reduction.

FIG. 1C is a profile of unreduced glycopeptides from peaks 2-4, as shown in FIG. 1A, that were immunoprecipitated with monoclonal antibody 'C2 (lanes 2-4) and then monoclonal antibody 'E10 (lanes '2-'4). The precipitates were examined by electrophoresis without reduction.

FIG. 1D is a profile of reduced glycopeptides from peaks 1-4, as shown in FIG. 1a, that were examined by electrophoresis after reduction.

FIG. 1E is a profile of reduced glycopeptides from peaks 2-4, as shown in FIG. 1A, that were immunoprecipitated with monoclonal antibody 'C2 (lanes 2-4), and then monoclonal antibody 'E10 (lanes '2-'4). The precipitates were examined by electrophoresis after reduction.

DETAILED DESCRIPTION OF THE INVENTION

EXAMPLE I

Figure 1A:
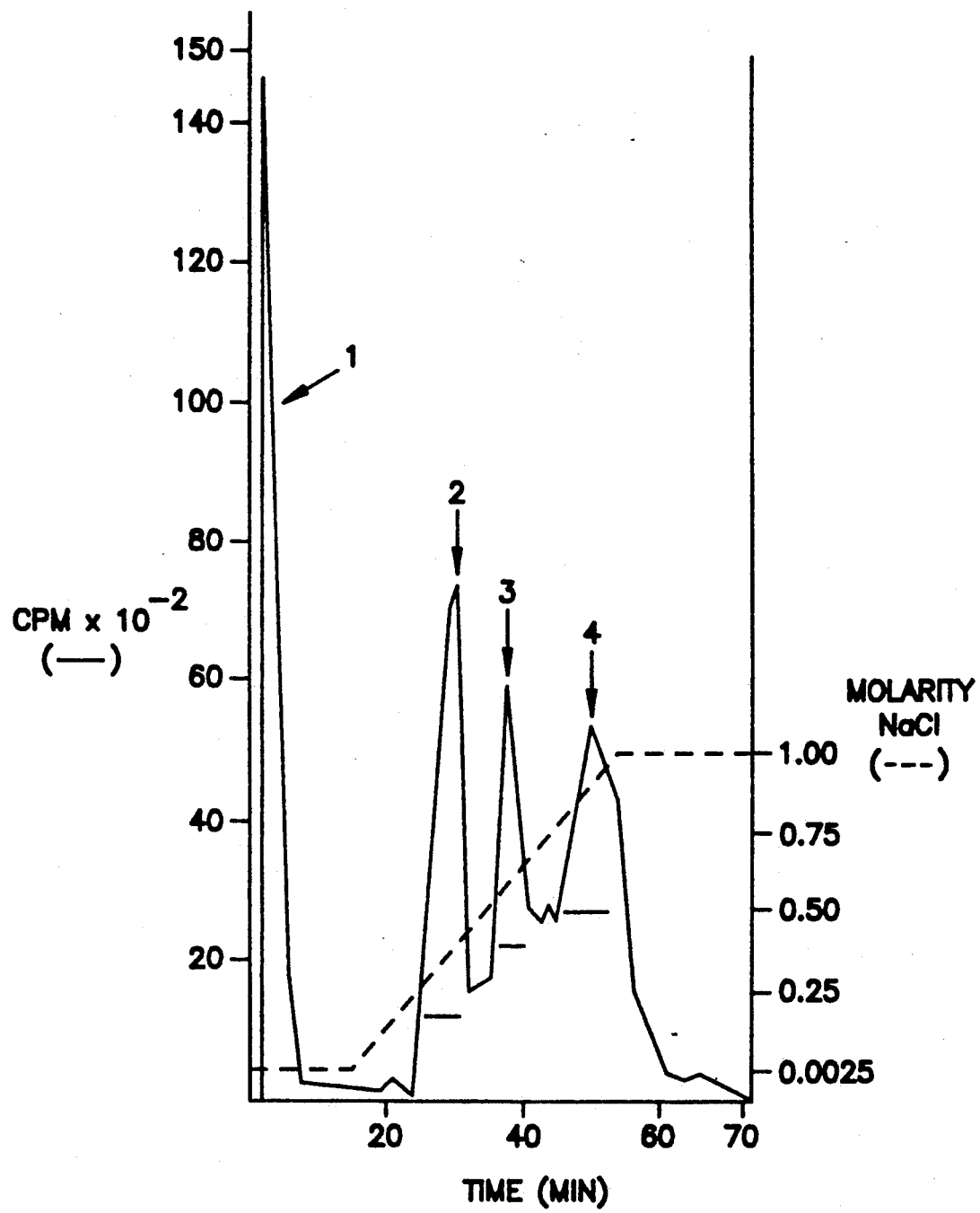
FIGS. 1A-1E. Unreduced detergent extracts of HCMV Towne strain were fractionated by ion-exchange HPLC. The retained peaks 2-4, which contained glycopeptides and glycopeptide complexes, were examined for their reactivity to the monoclonal antibodies. Lane numbers in FIGS. 1B-1E, indicate the ion-exchange peak, as shown in FIG. 1A, from which the sample was obtained. Numbers to the right of each figure are molecular weights times $10^{-3}$. The glycopeptides were detected by fluorography.

Growth of Virus and Purification of Glycopeptide

A. Materials and Methods

1. Growth, Radioactive Labeling, and Purification of Virus

Human primary fibroblast cultures grown in Dulbecco's Modified Eagle's Medium (DMEM) plus 10% fetal bovine serum were infected with Towne strain HCMV at an multiplicity of infection (MOI) of 1-5. At 1-2 days post infection [$^3$H]glucosamine (5 uCi/ml, 22 Ci/mM, Amersham, Arlington Heights, Ill.) or [$^{35}$S]methionine (5 uCi/ml, 109 Ci/ mM, DuPont/NEN, Boston, Mass.) was added as a marker during subsequent purification.

Cells and cellular debris were removed from the medium by low speed centrifugation at 7500×g for 20 minutes. Virus was collected from the supernatant by centrifugation at 48,200×g for 1 hour. The viral pellet was resuspended in Tris NaCl buffer (50 mM trishydroxymethylamino methane-HCl, pH 7.4, and 150 mM NaCl) and layered onto 20-60% sucrose gradients made with the same buffer. Velocity sedimentation was done at 131,300×g for 1 hour. Gradients were collected and monitored for optical density at 280 nm. A major peak of optical density which banded at 43% sucrose was collected. These fractions were diluted with Tris NaCl buffer and virus collected by centrifugation at 131,300×g for 2 hours. This purified whole virus preparation was designated "Purified Towne Prep."

2. Detergent and Chloroform Methanol Extraction

Virus detergent extracts were prepared by suspending 10-15 mg of purified virus in 3-5 ml of Tris NaCl buffer (50 mM Tris HCl, pH 7.5, 10 mM NaCl and 2 mM PMSF) containing 1.0% Nonidet P-40 (NP-40, polyoxyethylene-p-t-octylphenol). Detergent-virus suspensions were stirred for 1 hour at room temperature at which time extracted proteins were separated from insoluble proteins by high speed centrifugation for 1 hour. In some cases, purified virus was extracted with chloroform:methanol (2:1, v/v) prior to extraction with detergent to remove lipids. One volume of virus suspension in Tris NaCl buffer was extracted with 20 volumes of chloroform:methanol by stirring at room temperature for 20 minutes, followed by centrifugation to separate phases and collect delipidated proteins.

3. Isolation of HCMV Disulfide-linked Glycopeptide Complexes by Ion-Exchange HPLC Disulfide-linked glycopeptide complexes were isolated by anion-exchange high performance liquid chromatography. Separation was achieved using a Varian Model Vista 5500/402 HPLC system consisting of pump, gradient former and UV detector.

For anion exchange chromatography, 0.5 ml of unreduced detergent extract was applied directly to an Aquapore AX-300 anion exchange column (Brownlee Labs Inc., Santa Clara, Calif.). The column was washed for 15 minutes with 20 mM Tris-HCl buffer, pH. 7.8 containing 2.5 mM NaCl and 0.1% NP-40. Bound glycopeptides were eluted with a 40-minute linear gradient of NaCl from 2.5 mM to 1.0M in the same buffer as initially used. The column was washed for an additional 15 minutes at 1.0M NaCl to elute all bound glycopeptides. The flow rate was 1 ml/minute. Fractions collected were monitored for radioactivity.

4. Immunoprecipitation

For immunoprecipitation, Protein A-Sepharose CL-4B beads (Sigma-Aldrich, St. Louis, Mo.) were prepared by incubation with goat anti-mouse IgG (H and L) and washed with phosphate-buffered saline (PBS) before use. Whole extract or glycopeptides and glycopeptide complexes obtained by ion-exchange HPLC were incubated with either monoclonal antibody 1-48-41C2, 2-29-9B7 or 2-15-9E10 (preparation, infra) in PBS containing 0.1% NP-40 for 1.5 hours with constant mixing. In some cases, 0.1% sodium dodecylsulfate (SDS) was used in place of NP-40. The prepared Protein A-Sepharose CL-4B beads were then added to the antigen-antibody solution and allowed to react for an additional 1.5 hours with constant mixing. The beads were washed three times with PBS containing 0.1% NP-40. Following the final wash, proteins associated with the beads were solubilized for SDS-PAGE.

5. Preparation of Monomer

Isolated HCMV disulfide-linked glycopeptide complexes were reduced by addition of dithiothreitol to a final concentration of 10 mM (DTT, U.S. Biochemicals, Cleveland, Ohio) in the presence of 8M Urea. The reaction was allowed to proceed at room temperature for 2-24 hours with constant stirring. Alkylation of the reduced sulfhydryl group was done by adding 5-10 mg iodoacetamide and allowing the reaction to proceed at room temperature for an additional hour.

6. Gel Filtration HPLC of Individual HCMV Glycopeptides

Samples containing 1% SDS were subjected to gel filtration HPLC using the Varian system described above. Gel filtration was performed coupling TSK 3000 SW and 4000 SW gel filtration columns (Toyo Soda, Tokyo, Japan) in series and eluting isocratically with 50 mM sodium phosphate, pH 7.0, containing 0.1% SDS. The flow rate was 0.3 ml/minute. Absorbance was monitored at 275 nm and fractions collected were also monitored for radioactivity.

7. SDS-Polyacrylamide Gel Electrophoresis and Fluorography

SDS-PAGE was done with 5-15% polyacrylamide slab gel gradients following the method of Laemmli. Samples were solubilized by boiling for three minutes in the presence of 4% SDS. After the samples were cooled to room temperature, urea and beta-mercaptoethanol (BME) were added so that samples contained 5% BME and 2M urea. Tritium was detected by fluorography using Enlighting (DuPont/NEN, Boston, Mass.).

B. Results

1. Isolation of HCMV Glycopeptide Complexes by Ion-Exchange HPLC

Figures 1B, 1C:
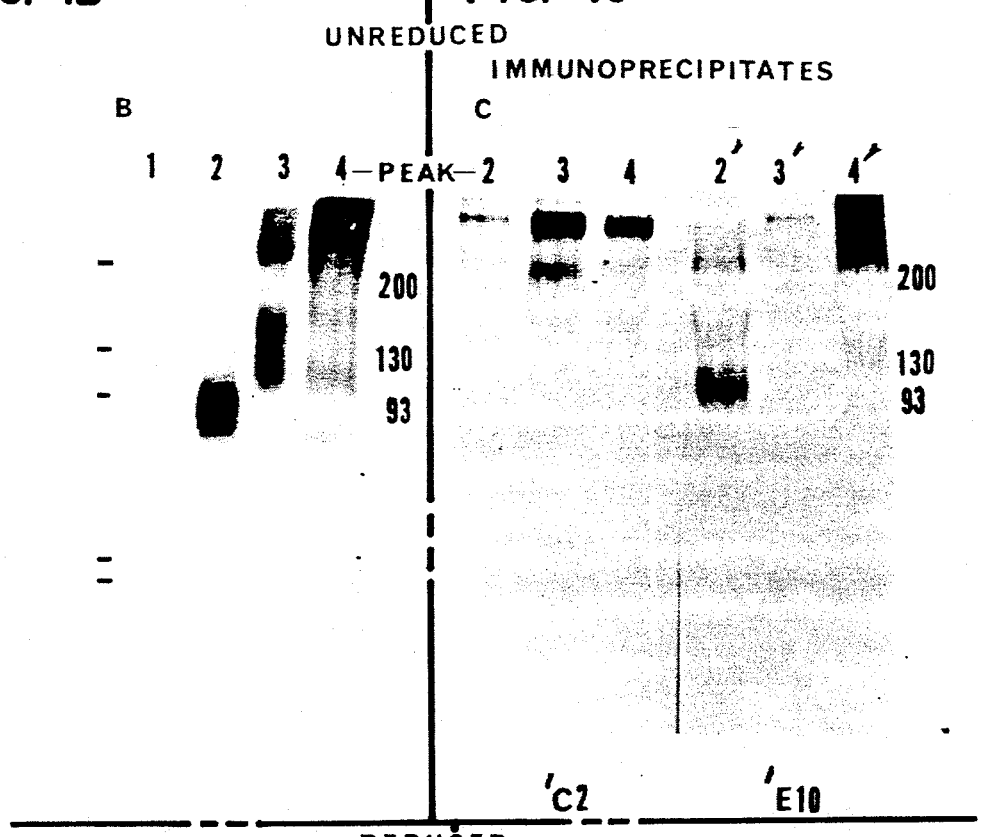
Figures 1D, 1E:
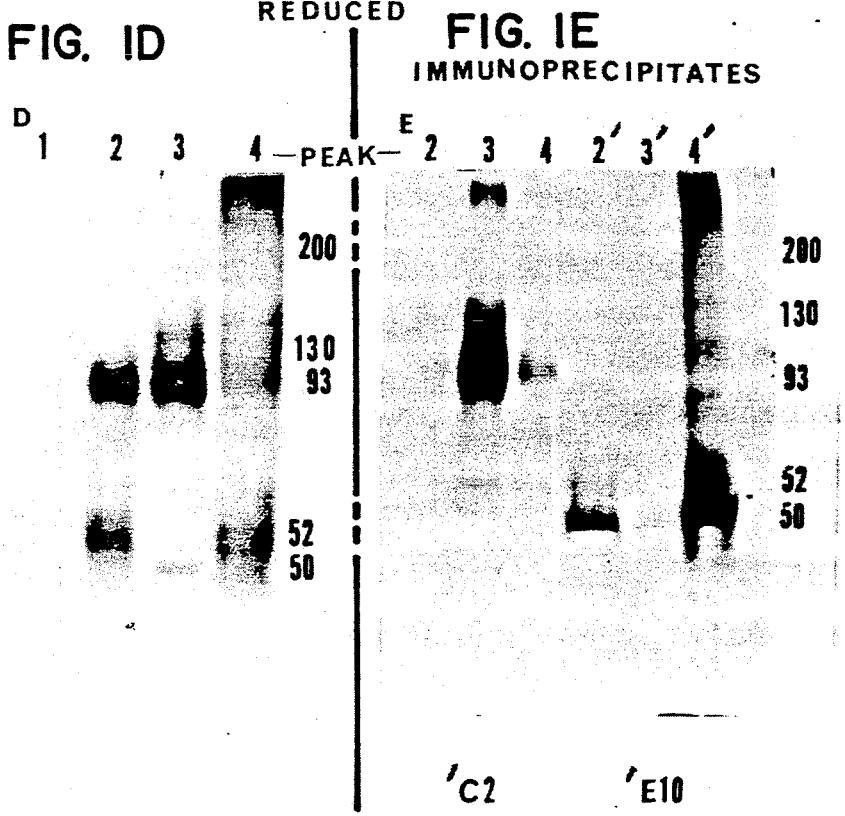

It has been known that HCMV contains disulfide-linked glycopeptides which react with monoclonal antibodies. It was of interest to determine if ion-exchange HPLC could be used to separate these or other disulfide-linked glycopeptides of HCMV. When unreduced [$^3$]glucosamine labelled detergent extracts of HCMV were separated by ion-exchange HPLC, one unretained peak and three retained peaks of radioactivity were detected (FIG. 1 A). The unretained peak contained material which could be extracted into chloroform:methanol (2:1,v/v) and could not be fixed in polyacrylamide gels using conditions which fix proteins (lane 1, FIG. 1 B, D). Moreover, this material could not be labelled with [$^{35}$S]methionine (data not shown). Based on these results, it was concluded that this peak contained glycolipid. The glycolipids were not examined for reactivity to the monoclonal antibodies.

While the unretained peak contained little or no glycopeptide, the three retained peaks did contain disulfide-linked glycopeptides (FIG. 1 B, D). This was determined by examining material from each of the retained peaks by electrophoresis with and without reduction of disulfide bonds. Examination of peak 2 by electrophoresis without reduction showed that it contained one abundant band with an apparent molecular weight of 93,000. However, after reduction of disulfide bonds, at least two glycopeptides were detected with apparent molecular weights of 50-52,000 and 93,000 (lane 2, FIG. 1 B, D). Thus, peak 2 appeared to contain a glycopeptide complex with a molecular weight of 93,000 and a glycopeptide with a similar apparent molecular weight. Peaks 3 and 4 also contained disulfide-linked glycopeptide complexes. When material from peak 3 was examined by electrophoresis without reduction, two major bands were detected. One band was observed at the top of the resolving gel and the second major band covered molecular weights of 130-180,000. After reduction of this material, three glycopeptides were detected (lane 3, FIG. 1 B, D). The most abundant species had an apparent molecular weight of 93,000, while two less-abundant species had molecular weights of 50,000 and 130,000. Analysis of peak 4 by electrophoresis without reduction showed that the most abundant material in this peak had a molecular weight greater than 200,000 and formed a smear at the top of the resolving gel (lane 4, FIG. 1 B). However, there was material in this peak which had a molecular weight similar to that observed for material in peak 3. This was most likely present because of tailing of peak 3 into peak 4. Finally, when peak 4 was examined by electrophoresis after reduction of disulfide bonds, lower molecular weight glycopeptides were detected (lane 4, FIG. 1 D). Of the most abundant species, one had an apparent molecular weight of 50-52,000, while another species had an apparent molecular weight of 90-130,000. However, even after reduction, some material in peak 4 still formed a smear at the top of the resolving gel.

2. Immunogenicity of the Isolated Glycopeptide Complexes Examined by Reactivity with Monoclonal Antibodies Monoclonal antibodies were made as described in the second example of this invention. Material from the three retained peaks from ion-exchange was examined for reactivity with MoAbs 2-29-9B7 ('B7), 1-48-41C2 ('C2) and 2-15-9E10 ('E10). Equal amounts of radioactivity were used from each peak for immunoprecipitation. It was determined that 'B7 and 'C2 reacted most strongly with the disulfidelinked glycopeptide complexes found in peak 3, precipitating 19 times more radioactivity from this peak than peak 2 and 6 times more radioactivity when compared to peak 4. These complexes, when reduced, appeared to contain all the glycopeptides detected in peak 3 (FIG. 1, Lane 3, C and E). Among these glycopeptides was the most abundant glycopeptide, which had a molecular weight of 93,000.

Unlike 'B7 or 'C2, 'E10 reacted most strongly with peak 4, precipitating 5-6 times more radioactivity from this peak than peak 2 and 11-12 times more radioactivity than from peak 3. However, while 'E10 did react most strongly with the glycopeptide complexes found in peak 4, it also reacted with the 93,000 molecular weight glycopeptide complex found in peak 2 which generated glycopeptides with molecular weights of 50-52,000 after reduction of disulfide bonds (FIG. 1, Lanes 2 and 4, C and D). Moreover, the glycopeptide complexes immunoprecipitated from peak 4 also contained glycopeptides with molecular weights of 50-52,000 as the most abundant species when the complexes were examined after reduction of disulfide bonds. However, while the 50-52,000 molecular weight glycopeptides were the most abundant species in glycopeptide complexes from peak 4, there were still a number of other glycopeptides detected after reduction of disulfide bonds. In fact, the complexes immunoprecipitated by 'E10 appeared to contain most or all of the glycopeptides detected in peak 4.

Most of the glycopeptides detected in peaks 2-4 were found in complexes reactive with either 'B7 and 'C2, or 'E10. However, the 93,000 molecular weight glycopeptide detected in peak 2 did not appear to react with any of the antibodies even though there was a significant amount of this glycopeptide present. This suggested that this glycopeptide was different from the 93,000 molecular weight glycopeptide detected in peaks 3 and 4. To further examine this possibility, material from peak 2 was immunoprecipitated first with 'C2 and then 'B7 using approximately a 15-fold excess of antibody. Protein A sepharose beads were added several times until no more radioactivity could be immunoprecipitated. The supernatant obtained after these precipitations was immunoprecipitated with 'E10 following the same procedure. After the final immunoprecipitation, the material left in the supernatant was examined by electrophoresis. When this was done, the 93,000 molecular weight glycopeptide was the only glycopeptide detected.

3. Glycopeptides Reactive with the Monoclonal Antibodies

When material from any one of the three ionexchange peaks was immunoprecipitated, under non-reducing conditions, with any one antibody, several bands were routinely detected. After reduction, these various complexes gave rise to a number of lower molecular weight glycopeptides. Because of this, it was determined whether reduction prior to immunoprecipitation would affect the number or relative amount of the various glycopeptides immunoprecipitated. To examine antibody reactivity to individual glycopeptides, material from each ion-exchange peak was reduced with DTT in the presence of 8M urea and 0.1% NP-40. After reacting overnight, glycopeptides were alkylated by addition of iodoacetamide. As a control experiment, whole extract, which contained all the various disulfide-linked glycopeptides, was reduced under the same conditions and examined by electrophoresis without further reduction with BME. When this was done, the majority of the glycopeptides were detected in bands with molecular weights of 50-52,000 and 90-92,000. This suggested that the reduction done with DTT was effective. Based on radioactivity, equal amounts of reduced and unreduced material from peaks 2 and 4 were immunoprecipitated with 'E10 while reduced and unreduced material from peak 3 was immunoprecipitated with 'C2. When reduced material was immunoprecipitated, the amount of radioactivity precipitated was decreased 2- to 3-fold when compared to the amount precipitated from unreduced material. This occurred with both antibodies. However, the number of glycopeptides immunoprecipitated was not affected. Furthermore, densitometric scans demonstrated that the relative amounts of the glycopeptides immunoprecipitated were not affected by reduction prior to immunoprecipitation. These results suggested that the glycopeptides found in the various disulfidelinked complexes were immunologically related.

4. Further Purification of Individual Immunogenic HCMV Glycopeptides

Figure 2:
FIG. 2 is a profile of glycopeptides GLP-A and GLP-B, purified by a combination of HPLC and immunoaffinity methods, that were immunoprecipitated with monoclonal antibodies to demonstrate retention of immunogenicity. Lane 1 shows glycopeptide GLP-A immunoprecipitated with monoclonal antibody 'C2, and lane 2 shows glycopeptide GLP-B immunoprecipitated with monoclonal antibody 'E10.
Figure 2:

By ion-exchange HPLC, we were able to purify immunogenic glycopeptide complexes, but not individual glycopeptides. Furthermore, it was clear that the monoclonal antibodies would react with several glycopeptides. Thus, it was not possible to obtain individual glycopeptides by either ion-exchange HPLC or immunoaffinity methods alone. Therefore, to obtain individual immunogenic HCMV glycopeptides, a purification method was developed which combined ion-exchange HPLC, immunoaffinity purification, and separation by gel filtration HPLC. To obtain the most abundant immunogenic glycopeptides, GLP-A and GLP-B, disulfide-linked glycopeptide complexes were first separated by ion-exchange HPLC. Glycopeptide complexes containing GLP-B found in peaks 2 and 4 were then further purified by immunoaffinity methods using monoclonal antibody 'E10 while those containing GLP-A in peak 3 were further purified using monoclonal antibody 'C2. Glycopeptide complexes purified by these methods were then reduced with DTT and alkylated with iodacetamide to generate individual glycopeptides. To obtain the 93,000 molecular weight glycopeptides from peak 2, which was not reactive with any monoclonal antibody, the supernatant obtained after immunoprecipitation of peak 2 with both 'C2 and 'E10 was also reduced and alkylated. The individual glycopeptide thus produced were then subjected to gel filtration HPLC. Glycopeptides obtained in this manner were examined by SDS-PAGE and shown to be individual glycopeptides. The glycopeptide recognized by 'E10 was denoted GLP-B; that recognized by 'C2 was denoted GLP-A. In addition, the major glycopeptides recognized by monoclonal antibodies 'E10 and 'C2 and purified by this method could still be immunoprecipitated by these antibodies, suggesting that the glycopeptides maintained their immunogenicity through the final step of purification (FIG. 2).

EXAMPLE II

Monoclonal Antibodies to GLP-A and GLP-B

A. Materials and Methods

1. Generation and Purification of Monoclonal Antibodies

Monoclonal antibodies were generated by using Purified Towne Prep. as the antigen. Adult BALB/C mice were immunized intraperitoneally with antigen emulsified in complete Freund's adjuvant, followed with three booster immunizations using saline-suspended immunogen given at three-week intervals. Three days following the final booster, the mouse was sacrificed and the spleen cells fused with SP2/0-Ag14 myeloma cells (American Tissue Culture Collection) at a ratio of 4:1 using polyethylene glycol. Twenty-four hours later, the fused cells were distributed into 96 wells in Hepes-buffered Dulbecco's modified Eagle's medium (DMEM) supplemented with 10% fetal bovine serum, 50 µg/ml garamycin, 13.6 µg/ml hypoxanthine, 0.4 µM aminopterin and 7.6 µg/ml thymidine. After two weeks in this medium, the cells were transferred to new medium supplemented as above but without aminopterin. Three to four weeks after cell fusion, supernatants from these cultures were assayed for antibodies specific to HCMV NP-40 extract by the ELISA assay. Cloning of cells from positive cultures was performed by limiting dilution using mouse thymocytes as feeder cells. Individual wells were screened microscopically for single colonies and assayed for antibody to HCMV NP-40 extract as above. Antibodyproducing clones were expanded for production of ascites fluid in BALB/c mice.

2. Neutralization Assays

Monoclonal antibodies purified by hydroxylapatite HPLC were diluted in DMEM supplemented with 2% fetal bovine serum (FBS). Prior to infection, 600 plaque-forming units (pfu) of Towne and 300 pfu of Toledo strain CMV were added to monoclonal antibody in a total volume of 0.4 ml of DMEM. Guinea pig complement (Pel-Freeze Biologicals, Rogers, Ark.) was added to a final concentration of 2.0% in half the preparations; the remaining half received an equivalent volume of DMEM. Viral neutralization was left to proceed for 60 minutes at 37° C. The HCMV-monoclonal antibody mixture was added to confluent layer of skin fibroblasts in 6-well plates (Costar, Cambridge, Mass.) and incubated for another 60 minutes for the virus to adsorb. The virus mixture was aspirated and 5 ml of DMEM supplemented with 2% FCS, garamycin, penicillin G and 0.5% agarose (Sea Plaque, FMC Co., Rockland, Md.) was added to each well. On day 8, the monolayers were fixed with 10% formalin in 70% ethanol, stained with methylene blue and the plaques counted. Viral neutralization was evaluated using the formula:

$$\% \text{ Plaque Reduction} = \frac{\text{Avg. Max. } pfu - \text{test } pfu \times 100}{\text{Avg. Max. } pfu}$$

and is reported as the protein concentration required for a 50% reduction in plaque numbers.

3. Purification of Monoclonal Antibodies

Monoclonal antibody from ascites was purified by high-performance hydroxylapatite chromatography, according to Juarez-Salinas (H. Juarez-Salinas et al., *Biotechniques*, May/June 1984), the teaching of which is hereby incorporated by reference.

4. Immunofluorescence

Adenovirus, HSV, VZV, and the wild type HCMV were obtained from clinical isolates. For immunofluorescence, infected and uninfected skin fibroblast cultures on glass slides were fixed in cold acetone:methanol (v/v, 1:1). Fixed cultures were preincubated with normal porcine serum and washed with phosphate-buffered saline (PBS). All subsequent steps were done with PBS containing 0.1% NP-40. Cultures were incubated with HPLC-purified ascites monoclonal antibody or with tissue culture fluid for 30 minutes and washed with PBS NP-40 buffer. Cultures were then incubated with fluorescein isothiocyanate (FITC) labeled goat antimouse IgG (Cappel, Malvern, Pa.). Following a final wash, slides were examined with a Zeiss phase fluorescence microscope.

5. Immunoprecipitation

For immunoprecipitation protein A sepharose CL-4B beads (Sigma-Aldrich, St. Louis, Mo.) were prepared by incubation with goat antimouse IgG (H and L) and washed with phosphate-buffered saline (PBS) before use. Whole extract or glycopeptides and glycopeptide complexes obtained by ion-exchange HPLC were incubated with either monoclonal antibody 'C2, 'B7, or 'E10 in PBS containing 0.1% NP-40 for 1.5 hours with constant mixing. In some cases, 0.1% SDS was used in place of 0.1% NP-40. The prepared protein A sepharose CL-4B beads were then added to the antigen antibody solution and allowed to react for an additional 1.5 hours with constant mixing. The beads were washed three times with PBS containing 0.1% NP-40. Following the final wash, proteins associated with the beads were solubilized for SDS-PAGE.

B. Results

1. Glycopeptides Recognized by Groups A and B MoAbs

Monoclonal antibodies were obtained which reacted with the glycopeptide bands. Based on reactivity, they could be classified into two groups, A and B. MoAbs 2-29-9B7 ('B7) and 1-48-41C2 ('C2) were representative of Group A. MoAb 2-15-9E10 ('E10) was representative of Group B. Since HCMV contained disulfide-linked glycopeptide complexes, monoclonal antibodies were used to immunoprecipitate both reduced and unreduced crude detergent extracts to determine if glycopeptides precipitated because they were recognized by the antibodies or if any glycopeptides precipitated because they were associated by disulfide bonds to other glycopeptides which were recognized by the antibodies. Therefore, part of an NP-40 extract of Towne strain HCMV was reduced with DTT and all available sulfhydryl bonds alkylated with iodoacetamide to prevent re-polymerization. Extracts reduced in this manner were examined by electrophoresis to assure that they had been reduced. All 3 antibodies were used to immunoprecipitate both reduced and unreduced extract as described in materials and methods. MoAbs 'B7 and 'C2 immunoprecipitated one abundant glycopeptide which formed a broad band with an approximate molecular weight of 93,000. In addition, there were 3 lessabundant glycopeptides with molecular weights of 130,000, 52,000 and 50,000. The numbers and molecular weights of glycopeptides precipitated were not affected by reduction prior to immunoprecipitation. However, while the relative amounts of most glycopeptides were also unaffected, there was some difference in the intensity of the 50,000 to 52,000 molecular weight glycopeptides immunoprecipitated by 'C2 after reduction.

Examination of 'E10 immunoprecipitates showed that the pattern of glycopeptides immunoprecipitated was very different when compared to that obtained with 'B7 and 'C2. When 'E10 was used, one abundant glycopeptides could be detected with approximate molecular weight of 50,000 to 52,000. Both these glycopeptides formed broad bands in the gel. However, there were also at least 4 less-abundant glycopeptides with molecular weights of 90–93,000, 116,000, and 130,000 as well as some material which had a molecular weight greater than 200,000 and smeared at the top of the gel. However, like 'B7 and 'C2, the pattern of glycoproteins and the relative amounts precipitated by 9E10 was not affected by reduction prior to precipitation.

2. Neutralization and Immunofluorescent Staining of Infected Cells with Monoclonal Antibodies of Groups A and B Neutralization of HCMV strains Towne and Toledo by 'E10 did not require the addition of complement, whereas 'B7 at similar concentrations (less than 10 ug/ml) was dependent upon the addition of 2% guinea pig complement (Table 1). However, at higher concentrations (greater than 30 ug/ml) 9B7 could neutralize virus in the absence of complement. In the presence of 2% guinea pig complement, 'C2 did neutralize Toledo (Table 1), but required much higher antibody concentrations to neutralize this strain in the absence of complement. Furthermore, this antibody did not display any neutralizing activity against strain Towne at antibody concentrations less than 200 ug/ml.

TABLE I

| In Vitro Neutralization cf HCMV Laboratory Strains Towne and Toledo Microgram per ml for 50% PFU reduction | | | | |
|---|---|---|---|---|
| HCMV Strain: | TOWNE* | TOWNE | TOLEDO* | TOLEDO |
| Monocolonal Antibody | +c' | −c' | +c' | −c' |
| 9E10 | 4 | 8 | 4 | 10 |
| 41C2 | >200 | >200 | 2 | 100 |
| 9B7 | 2 | 36 | 2 | 48 |

*Average number of PFU in control cultures were 600 for Toledo and 300 for Towne when inoculated with virus and complement, but no antibodies.

The MoAbs were also examined for their reactivity to skin fibroblast cells infected with HCMV laboratory and wild type strains as well as Herpes Simplex (HSV), Varicella zoster (VZV), Epstein Barr virus (EBV) and adenovirus. Both MoAbs 'B7 and 'C2 were found to be specific to HCMV infected cells, reacting with both laboratory and wild type strains, but not with HSV, VZV, EBV or adenovirusinfected cells (Table 2). However, MoAbs 'E10 reacted with HCMV-infected cells and reacted with HSV-a and adenovirus-infected cells, but not with VZV-infected cells. All three antibodies were non-reactive to control skin fibroblast cells.

TABLE 2

| Antibody | Class | Reactivity of Monoclonal Antibodies to Infected Cells Immunofluorescence* | | | | | | | | | |
|---|---|---|---|---|---|---|---|---|---|---|---|
| | | Towne | AD169 | A# | B | C | D | HSV | Adenovirus | VZU | EBV | SF |
| Control |
| 9E10 | IgG3 | ++ | + | + | + | ND | ND | + | ++@ | — | ND | — |
| 41C2 | IgG2b | ++ | +.+ | ++ | ++ | ++ | ++ | — | — | — | — | — |
| 987 | IgG1 | ++ | ++ | ++ | ++ | ++ | ++ | — | — | — | — | — |

*Cytoplasmic immunofluorescence of acetone-methanol fixed, CMV-, HSV-, adenovirus-, and VZU-infected human skin fibroblasts (SF) was performed as described under materials and methods.
A-D are HCMV clinical isolates.
@Monoclonal antibody 9E10 also reacted with adenovirus grown in Hep2 cells. Uninfected Hep2 cells were negative.
ND, Not Done.

3. Reactivity of Isolated glycopeptides and Glycopeptide Complexes with MoAbs 'E10, 'B7 and 'C2

The glycopeptides immunoprecipitated by the MoAbs were not affected by reduction prior to immunoprecipitation. Therefore, it was desirable to determine the relatedness of the glycopeptides, both associated in the complexes by disulfide bonds and those which were not. Equal amounts of radioactivity from peaks 2–4 were collected and serially immunoprecipitated with 'C2 and 'B7, and then 'E10. When fractions from peaks 2–4 were immunoprecipitated with 41C2, it was observed that this antibody reacted most strongly with material from peak 3, precipitating 19 times more radioactivity from peak 3 than peak 2 and 6 times more radioactivity when compared to peak 4 (See FIG. 1).

After immunoprecipitation with 'C2 or 'B7, the ion-exchange fractions were immunoprecipitated with monoclonal antibody 'E10. Immunoprecipitation with this monoclonal antibody showed that it reacted most strongly with peak 4, precipitating 5–6 times more radioactivity from this peak than peak 2 and 11–12 times more radioactivity than from peak 3. When 'E10 immunoprecipitates from peak 2 were examined by electrophoresis without reduction of disulfide bonds, a 93,000 molecular weight band was detected as well as two less intense bands with molecular weights of 140,000 and 180,000. This pattern was very similar to what was observed when material from peak 2 was examined by electrophoresis without reduction. When 'E10 immunoprecipitates of peak 2 were examined by electrophoresis after reduction, glycoproteins with molecular weights of 50-52,000 were detected as well as a very small amount of glycopeptide with a molecular weight of 90,000. However, no 93,000 molecular weight glycopeptide was detected. Immunoprecipitates from peak 3 contained very little radioactivity. Unreduced, this material was in high molecular weight bands and most of the radioactivity was detected in a glycopeptide with a molecular weight of 50,000 after reduction. However, a very small amount of a 93,000 molecular weight glycopeptide was also detected in immunoprecipitates from peak 3.

It was interesting to note that most of the glycopeptides detected in peaks 2–4 reacted with either 'B7 and 'C2, or 'E10. However, the 93,000 molecular weight glycopeptide detected in peak 2 did not appear to react with any of the antibodies even though there was a significant amount of this glycopeptide present. This suggested that this glycopeptide was different from the 93,000 molecular weight glycopeptides detected in peak 3. To further examine this possibility, material from peak 2 was immunoprecipitated first with 'C2 and then 'B7 using approximately a 15-fold excess of antibody. Protein A sepharose beads were added several times until no more radioactivity could be precipitated. The supernatant obtained after these precipitations was immunoprecipitated with 'E10 following the same procedure. After the final immunoprecipitation, the material left in the supernatant was examined by electrophoresis. When this was done, the 93,000 molecular weight glycopeptide was the only glycopeptide detected. The results of these assays are summarized on Table 3, below.

TABLE 3

| | Glycopeptide Complexes and Glycopeptides Immunoprecipitated by MoAbs | |
|---|---|---|
| Ion-Exchange HPLC Peak* (MoAb Reactivity) | Glycopeptide Complex Immunoprecipitated (mol wt., Kd) | Glycopeptides Immunoprecipitated After Reduction (mol wt., Kd) |
| 2 (9E10) | 93 | 50–52 |
| 4 (9E10) | 450 | 50–52, 90, 116, 130, >200 |
| 3 (41C2, 9B7) | 10, and >130 | 50–52, 93, 10 |
| 2 (none) | 93 Kd Glycopeptide not Associated in Disulfide-linked Complex | 93 Kd Glycopeptide not Immunoprecipitated by any MoAb |

*FIG. 1

EXAMPLE III

Stimulation of Human Cellular Immunity

A. Materials and Methods

1. Isolation of HCMV-Specific T Cell Blasts

HCMV-specific T cell blasts were prepared in 25 cm$^2$ upright tissue culture flasks by stimulating $10 \times 10^6$ fresh peripheral blood monocytes (MNC) at a concentration of $1 \times 10^6$ MNC/ml with 10.0 μg of heat-inactivated HCMV antigen (Purified Towne Prep., 56° C./1 hr) suspended in RPMI 1640 medium in 10% PHS. After six days at 37° C. in 5% CO2 atmosphere, the HCMV-specific blasts were cloned by limiting dilution in 96 well U-bottomed tissue culture plates at 0.3 cell/well in the presence of x-irradiated autologous MNC as feeder cells, heat-inactivated HCMV antigen (1 μg/ml), and 10–20% TCGF (Biotest, Frankfurt, Germany). Thereafter, cells were refed every 3–4 days with fresh TCGF-containing media. Weekly, HCMV antigen and autologous x-irradiated feeder cells were added to the media. After day 21, growing cells were fed and transferred to 24 well plates for further expansion and then reseeded into 25 cm² tissue culture flasks for large scale production. Some expanded clones were subcloned by a second limiting dilution to ensure clonality. Lines were developed from 4 different HCMV seropositive donors yielding more than 100 individual T-helper ($T_h$) cell clones.

2. Characterization of the HCMV-$T_h$ Clones

All $T_h$ clones were characterized as to phenotype, proliferative responses, IL-2 production, and cytotoxic activity as follows:

A. Phenotype analysis $T_h$ clones were analyzed for expression of OKT phenotypic determinants using the monoclonal antibodies OKT3 (total T cells), OKT4 (helper/inducer T cells), and OKT8 (cytotoxic/suppressor T cells) (Ortho Pharmaceuticals Inc., Raritan, N.J.) using an indirect immunofluorescence assay. Fluorescence was detected either by fluorescence microscopy using a Zeiss fluorescent microscope or flow cytometry using the EPICS541 (Coulter Corp., Hialeah, Fla.). All $T_h$ clones expressed the OKT3+ OKT4+ OKT8− phenotype.

B. Lymphocyte proliferation

T cell clones were rested in tissue culture media in the absence of TCGF overnight, and then restimulated for 72 hours with either HCMV antigen or a related herpes viral antigen, HSV, to determine the specificity of proliferation responses to HCMV. Responses to HSV were similar to tissue culture media background control. Thus, all $T_h$ clones were HCMV-specific.

C. Interleukin-2 (IL-2) production $T_h$ clones were stimulated with HCMV antigen, and the supernatants harvested at 24 hours and assayed for IL-2 activity using the murine CTLL-20 (IL-2 dependent) murine cell line. All $T_h$ clones were shown to produce IL-2, as seen by the survival and growth of CTLL-20.

D. Cytotoxic activity

All $T_h$ clones were tested for cytotoxic activity against the NK target cell line, K562, autologous uninfected and HCMV- and HSV-infected human skin fibroblasts as target cells. No NK or virus-specific cytotoxic activity was observed with any of the $T_h$ clones.

B. Evaluation of $T_h$ Cell Recognition of HCMV Immunogens

The early and key step in cellular immunity is recognition of the foreign antigen by the subpopulation of white blood cells (WBC) called T-helper ($T_h$) cells. The first immunogenic reactions of an antigen are dependent on its recognition by $T_h$ cells. After recognition, the $T_h$ cells are stimulated to proliferate and to produce lymphokines such as Il-2 which cause proliferation of several types of WBC. The relative proliferation of one of the HCMV-specific $T_h$ cell clones (WRC#3) by purified, unreduced glycopeptide complexes derived from HPLC peaks 2 ("2UR"), 3("3UR") and 4("4UR") is shown in Table 4.

TABLE 4

Proliferation of $T_h$ Cell Clone WRC#3

| Stimulant | ³H-thymidine incorporated (cpm) |
|---|---|
| WRC#3 (Control) | 95 ± 36 |
| WRC#3 + WRCMNC$^{IRR*}$ (Control) | 143 ± 10 |
| WRC#3 + WRCMNC$^{IRR}$ + HSV (1 μg/well) | 336 ± 92 |
| WRC#3 + WRCMNC$^{IRR}$ + Towne CMV (0.5 μg/well) | 55,080 ± 1,210 |
| WRC#3 + WRCMNC$^{IRR}$ + Triton X - 100 extract of Towne CMV (0.5 μg/well) | 9,311 ± 2,866 |
| WRC#3 + WRCMNC$^{IRR}$ + 2UR (0.1 μg/well) | 1,194 ± 792 |
| WRC#3 + WRCMNC$^{IRR}$ + 3UR (0.1 μg/well) | 19,706 ± 5,252 |
| WRC#3 + WRCMNC$^{IRR}$ + 4UR (0.1 μg/well) | 25,387 ± 389 |

*Irradiated MNC from donor WRC.

Importantly, antigen presented on the surface of adherent cells induces the clonal expansion of mononuclear lymphocytes that are directed specifically against the triggering antigen. After stimulation subsides, survivors of the expanded clone remain as memory cells in the body, ready to expand rapidly again when the same antigen is presented. The primary memory cells are $T_h$ cells.

GLP-A and GLP-B glycopeptides stimulate the memory WBC from seropositive but not seronegative donors as shown in Table 5. These results showed clearly that these glycopeptide complexes are an important immunologic component of HCMV.

TABLE 5

Proliferation of MNC from Seronegative and Seropositive Donors

| Stimulant | TL (CMV−) | JD (CMV+) | WRC (CMV−) | KM (CMV−) |
|---|---|---|---|---|
| Medium ("−" control) | 645 ± 145⁺ | 231 ± 67 | 312 ± 105 | 1,189 ± 635 |
| Staph phage lysate ("+" control for all doors) | 128,073 ± 26,856 | ND* | 267,167 ± 22,356 | 182,190 ± 22,747 |
| Towne Ag | 442 ± 94 | 109,262 ± 7,164 | 54,058 ± 10,157 | 31,224 ± 6,981 |
| 2UR | 983 ± 69 | 23,922 ± 1,714 | 3,592 ± 42 | 11,852 ± 2,423 |
| 3UR | 902 ± 45 | 9,277 ± 2,831 | 2,975 ± 1,792 | 39,088 ± 427 |
| 4UR | 1,144 ± 466 | 19,781 ± 2,889 | 1,865 ± 230 | 13,087 ± 1,268 |

*not determined.
⁺Mononuclear cells (MNC) isolated from heparinized blend of donors on Ficoll-Hypaque density gradients were assayed for lymphocyte proliferation by the method of R. C. Gehrz et al., J. Infect. Dis., 143, 391 (1981).

EXAMPLE IV

Diagnostic Assay for Human Cytomegalovirus Using Monoclonal Antibodies from Group A A. Materials and Methods Two monoclonal antibodies directed against different epitopes of the group A glycopeptides are used in this enzyme-linked immunoadsorbent assay. The primary or capture monoclonal antibody I is adsorbed onto a solid phase. The secondary monoclonal antibody II is conjugated to any indicator system which will give a read out. In the presence of HCMV, a positive read out will be obtained.

Capture antibody I, e.g. 'C2, was adsorbed onto Immulon I polystyrene microwells of the Removastrip system from Dynatech (Alexandria, Va.). A carbonate-bicarbonate buffer pH 9.5 was used and the wells were washed with phosphate-buffered saline pH 7.4 containing 0.05%-tween 20 (PBS-tween).

Purified CMV viruses and virus-infected or uninfected skin fibroblasts cell lysate obtained with PBS containing 1% NP-40 were added into the microwells and incubated for one hour at 37° C. The wells were then washed with PBS-tween.

Biotinylated monoclonal antibody II, e.g., 'B7 was added and the samples were incubated for one hour at 37° C. The wells were then washed with PSB-tween.

Streptavidin-conjugated to peroxidase (Kirkegaard & Perry Laboratories, Inc.) was added and the samples were further incubated for one hour at 37° C. The wells were then washed with PBS-tween and distilled water.

The substrate ortho-phenylenediamine in phosphate-citrate buffer, pH 5.0, was used with hydrogen peroxide added. After 15 minutes of incubation at room temperature, the reaction was stopped with 5N sulphuric acid. A Dynatech microwell plate reader was used to read the absorbence of the product at 490 n.m.

As shown in Table 5, the reaction with Towne strain of HCMV was linear above 7.8 nanograms total protein, while there was no measurable reaction with the skin fibroblast control. Patient samples were assayed directly and it was not possible to determine total virus protein. Table 6 shows a typical patient assay. AN HCMV-positive sample, verified by cell culture diagnosis, was shown to react strongly over background value.

TABLE 6

| | B. Results | |
|---|---|---|
| | Total Protein in (nanogram) | Absorbence at 490 n.m. |
| Sample HCMV Antigen | | |
| Towne Strain | 0 | 0.002 |
| | 0.5 | 0.051 |
| | 1 | 0.060 |
| | 2 | 0.088 |
| | 3.9 | 0.085 |
| | 7.8 | 0.110 |
| | 15.6 | 0.146 |
| | 31.3 | 0.211 |
| | 62.5 | 0.288 |
| | 125 | 0.430 |
| | 250 | 0.732 |
| | 500 | 1.379 |
| Patient Sample cell lysate | | |
| Skin Fibroblasts infected with HCMV (diluted 1/16) | | 1.967 |
| Uninfected Skin Fibroblasts | | 0.117 |
| HSV-1 Infected Skin Fibroblasts | | 0.101 |
| HSV-2 Infected Skin Fibroblasts | | 0.129 |

Patient samples were identified by classic cytopathic effect pattern recognition by trained clinical virology laboratory personnel.

DISCUSSION

We have discovered that HCMV contains at least two membrane envelope glycoprotein complexes which contain glycopeptides GLP-A, and GLP-B, which are arranged on the surface of the virus particle in such a way that they are neither encased in a fold, buried in a crypt nor sterically hindered from reacting with macrocomponents of the bodily environment, e.g., antibody and Th cell antigen recognition sites. These glycopeptides strongly elicit humoral and cellular immune responses, indicating a significant role in recovery from HCMV infection. Furthermore, MoAbs to these glycopeptides neutralize live viruses.

This invention provides a process for isolating microgram quantities of substantially pure glycopeptides. It is expected that GLP-A and GLP-B and the MoAbs derived therefrom will prove useful for the diagnosis of HCMV, therapy for infected patients and prophylaxis for uninfected persons.

MoAbs 1-48-41C2 and 2-29-9B7 are provided as examples of antibodies that can be raised against GLP-A. These antibodies are particularly useful for the diagnosis of active HCMV viruses. Those skilled in the art, following the teachings of this invention, may readily produce GLP-A to use in the identification of such monoclonal antibodies.

MoAb 2-15-9E10 is also provided which reacts with GLP-B and is capable of neutralizing HCMV without the addition of complement. Those skilled in the art, following the teachings of this invention, may readily produce GLP-B to use in the identification of other monoclonal antibodies which share this characteristic. Such antibodies are useful in HCMV therapy and the degree of cross reactivity with other viruses of the herpes class confers an additional advantage to this use.

The hybridomas producing the MoAbs provided as examples have been deposited with American Type Culture Collection (ATCC), Rockville, Md., and have been assigned the following accession numbers: Hb 2-29-9B7=HB 10925; Hb 2-15-9E10=HB 10926; and Hb 1-48-41C2=HB 10927.

Cultures of these deposited hybridomas will be made available to the public upon the grant of a patent based upon the present application. It is to be understood that the availability of a deposit does not constitute a license to practice the subject invention in derogation of patent rights granted by the U.S. Government.

While certain representations embodied are described herein for the purposes of illustration, it will be apparent to those skilled in the art that modifications therein may be made without departing from the spirit and scope of the invention.

We wish to thank Children's Hospital, St. Paul, Minn. for generous support and encouragement in this work.

What is claimed is:

1. A substantially-pure, immunogenic glycoprotein complex which is derivable from the membrane envelope of human cytomegalovirus, said complex having a molecular weight as determined by SDS-PAGE technique of about 93 kDa; the complex comprising at least two subunit glycoproteins each having a molecular weight of about 50 to 52 kDa, as determined by SDS-PAGE technique, the subunit glycoproteins being associated with each other in the complex by means of at least one disulfide bond; the complex with disulfide bond or bonds intact being immunoreactable with monoclonal antibody 9E10 produced by hybridoma IVI-10118, but not with monoclonal antibody 41C2 produced by hybridoma IVI-10119.

2. A substantially pure immonogenic glycoprotein which has a molecular weight of about 50 to 52 kDa as determined by SDS-PAGE technique, has at least one sulfhydryl group, is derivable from a glycoprotein complex having a molecular weight as determined by SDS-PAGE technique of about 93 kDa, which complex is obtained from the membrane envelope of human cytomegalovirus; and when within the complex, the glycoprotein is a subunit glycoprotein associated by means of at least one disulfide bond with one or more subunit glycoproteins having a molecular weight of about 50 to 52 kDa as determined by SDS-PAGE technique; the about 93 kDa glycoprotein complex with disulfide bond or bonds intact being immunoreactable with monoclonal antibody 9E10 produced by hybridoma IVI-10118, but not with monoclonal antibody 41C2 produced by IVI-10119.

3. The glycoprotein according to claim 2 which is produced by a process comprising reducing the disulfide linkages of a substantially pure, immunogenic glycoprotein complex which is derivable from the membrane envelope of human cytomegalovirus, said glycoprotein complex having a molecular weight of about 93 kDa as determined by SDS-PAGE technique.

* * * * *

UNITED STATES PATENT AND TRADEMARK OFFICE
CERTIFICATE OF CORRECTION

PATENT NO. : 5,248,768
DATED : September 28, 1993
INVENTOR(S) : Nancy O. Lussenhop et al.

It is certified that error appears in the above-identified patent and that said Letters Patent is hereby corrected as shown below:

At column 7, line 40, for "$[^3]$" read --$[^3H]$--.

At column 13, line 8, for "HSV-a " read --HSV- --.

At column 14, in Table 3 at line 41 for "10" (first and second occurrences) read --130--.

At column 16, in Table 5 (column headings) at lines 42-43, for "WRC     read   --WRC
        (CMV-)"         (CMV+)--.

At column 16, in Table 5 (column headings) at lines 42-43, for "KM     read --KM
        (CMV-)"         (CMV+)--.

At column 16, in Table 5 (line headings) at line 47, for "all doors)" read --all donors)--.

At column 16, in Table 5 (table footnotes) at line 53, for "$^+$" read --$^+$- --.

Signed and Sealed this

Nineteenth Day of July, 1994

BRUCE LEHMAN

*Attest:*

*Attesting Officer*     Commissioner of Patents and Trademarks